(12) United States Patent
Tybinkowski et al.

(10) Patent No.: US 6,721,388 B2
(45) Date of Patent: Apr. 13, 2004

(54) TILTABLE GANTRY FOR X-RAY TOMOGRAPHY SYSTEM

(75) Inventors: Andrew P. Tybinkowski, Boxford, MA (US); Michael J. Duffy, Methuen, MA (US); Lidia Nemirovsky, Salem, MA (US); Ronald E. Swain, Reading, MA (US)

(73) Assignee: Analogic Corporation, Peabody, MA (US)

( * ) Notice: Subject to any disclaimer, the term of this patent is extended or adjusted under 35 U.S.C. 154(b) by 23 days.

(21) Appl. No.: 10/151,270

(22) Filed: May 20, 2002

(65) Prior Publication Data

US 2002/0168044 A1 Nov. 14, 2002

Related U.S. Application Data

(63) Continuation-in-part of application No. 09/760,626, filed on Jan. 16, 2001.
(60) Provisional application No. 60/221,740, filed on Jul. 31, 2000.

(51) Int. Cl.[7] ................................................. H05G 1/60
(52) U.S. Cl. ........................................... 378/17; 378/15
(58) Field of Search ........................... 378/17, 15, 195, 378/193, 19, 20

(56) References Cited

U.S. PATENT DOCUMENTS

| 4,112,303 | A | | 9/1978 | Brandt .................... 250/445 T |
| 4,750,195 | A | * | 6/1988 | Takahashi .................... 378/15 |
| 4,797,008 | A | | 1/1989 | Helbig et al. .................. 384/49 |
| 4,798,540 | A | | 1/1989 | Bernardi ....................... 439/22 |
| 5,012,505 | A | | 4/1991 | Zupancic et al. ........... 378/130 |
| 5,071,264 | A | | 12/1991 | Franke et al. ............... 384/501 |
| 5,448,608 | A | | 9/1995 | Swain et al. .................... 378/4 |
| 5,799,054 | A | * | 8/1998 | Hum et al. .................... 378/17 |
| RE36,415 | E | | 11/1999 | McKenna ....................... 378/4 |
| 5,982,844 | A | | 11/1999 | Tybinkowski et al. ......... 378/4 |
| 6,337,894 | B1 | * | 1/2002 | Tybinkowski et al. ......... 378/4 |
| 6,452,998 | B2 | * | 9/2002 | Tybinkowski et al. ........ 378/17 |

* cited by examiner

*Primary Examiner*—David V. Bruce
*Assistant Examiner*—Iraki Kiknadze
(74) *Attorney, Agent, or Firm*—McDermott, Will & Emery (57) ABSTRACT

A frame for an x-ray tomography device allows a gantry of the frame to be tilted with a minimum applied force. The frame includes a stand including two substantially upright arms, a gantry positioned between and pivotally mounted to the arms of the stand for tilting about a tilt axis extending between the arms, a tilt guide secured to one of the gantry and the stand, and at least two spaced-apart wheels, each wheel operatively engaging the tilt guide such that turning the wheels applies a force to the tilt guide so that the gantry tilts about the tilt axis.

44 Claims, 12 Drawing Sheets

TILTABLE GANTRY FOR X-RAY TOMOGRAPHY SYSTEM

CROSS-REFERENCE TO RELATED APPLICATIONS

The present application is a continuation-in-part of U.S. patent application Ser. No. 09/760,626, filed Jan. 16, 2001, and claims priority from Provisional U.S. Patent Application Serial No. 60/221,740, filed Jul. 31, 2000, both of which are incorporated herein by reference in their entireties.

TECHNICAL FIELD OF DISCLOSURE

The present disclosure relates generally to x-ray tomography systems and, more specifically, to a tiltable gantry for x-ray tomography systems.

BACKGROUND OF DISCLOSURE

X-ray tomography systems have been used for many years to create images of cross-sectional slices of subjects, such as human patients, and are particularly used as a medical diagnostic aid. Computed tomography ("CT") scan systems usually include an annular gantry including an outer ring secured to a stand and an inner ring mounted for rotation within the outer ring about a centrally located spin axis of the gantry.

The gantry is typically about six (6) feet in diameter and the inner ring carries x-ray tomography components, which can include an x-ray tube for providing the x-ray beam, an anode for acting as the focal spot for the x-ray beam, one or more high voltage power supplies, balancing weights, a data acquisition module, and a bank of detectors diametrically opposed from the x-ray source, or focal spot. Some of these components may be secured in the outer ring of the gantry; however, at least some are secured in the inner ring for rotation therewith.

A platform, such as a patient table, is positioned horizontally through the center of the annular gantry, generally in alignment with the centrally located spin axis of the gantry, so that a subject to be x-rayed or scanned is supported on the table between the x-ray source and the bank of detectors. The inner ring of the gantry then rotates about the subject during the scanning procedure and the gantry may be adapted to move axially with respect to the table during and/or between successive rotations of the inner ring.

Often it is desirable to precisely tilt the gantry about a tilt axis normal to the spin axis so that the spin axis of the gantry is made parallel to, as well as aligned with, the subject to be scanned. Such tilting of the gantry is done to set a scan plane of the x-ray tomography system. However, because of the relatively large size and heavy weight of the gantry and the x-ray tomography components supported therein, precisely tilting the gantry to set the scan plane can be difficult.

Some older mechanisms for tilting the gantry of an x-ray tomography system simply comprise a pivot arm linked to the gantry at the location of the pivotal mounting of the gantry to the stand. The gantry is tilted by applying torque to the pivot arm. However, because of the considerable size and mass of the gantry, tilting the gantry in such a manner requires significant torque. The significant torque requirement in turn requires a powerful expensive mechanism for applying the torque. Furthermore, the significant torque requirement can cause unstable motion (e.g., rocking) of the gantry during tilting.

U.S. Pat. No. Re. 36,415 to McKenna, entitled "X-ray Tomography System with Gantry Pivot and Translation Control", shows an improved, portable x-ray tomography system wherein tilting movement of the gantry is precisely controlled by mechanical displacement means which, in turn, are coupled to electro-mechanical means for monitoring the amount of tilting.

In particular, McKenna shows an annular gantry pivotally secured at arms extending radially outwardly from the gantry such that the gantry can tilt about the arms. A short member has an end fixed to one of the arms, and a ball nut is secured to the other end of the member. The member and the ball nut remain stationary while allowing an elongated screw element to move through the ball nut as a reversible motor rotates the screw element. The motor is mounted on an outer frame of the gantry, close to the pivot arm, and the screw element is suitably journaled in the outer frame so that the screw element freely rotates without moving longitudinally with respect to the outer frame. As the screw element rotates, therefore, the entire outer frame (and therefore the entire gantry) tilts about the arms. The screw element is also journaled in the outer frame so that the screw element can pivot about the motor as the gantry tilts.

An x-ray tomography system having a tilting gantry, wherein a relatively small force is required to tilt the gantry, would be an advancement in the art. Preferably, such a system will provide stable, accurate, and precisely controlled tilting of the gantry.

SUMMARY OF DISCLOSURE

The present disclosure accordingly provides an apparatus that allows a gantry of an x-ray tomography device to be tilted with a minimum of applied force. The apparatus includes a tilt guide securable to one of the gantry and a stand of the x-ray tomography device, wherein the tilt guide is arcuate and has a center of curvature corresponding to a tilt axis of the gantry. The assembly also includes a drive mechanism securable to the other of the gantry and the stand. The drive mechanism has at least two spaced apart wheels, wherein each wheel operatively engages the tilt guide so that turning the wheels applies a substantially tangential force to the tilt guide to tilt the gantry about the tilt axis.

According to one aspect of the present disclosure, the apparatus includes a tilt lock movable against the tilt guide to hold the tilt guide in a fixed position. According to another aspect, the apparatus includes a tilt monitor providing a signal indicative of the amount of tilting. According to an additional aspect, the apparatus includes a tilt limiter for preventing further tilting upon reaching a predetermined maximum extent of tilt.

Other advantages of the presently disclosed frame with tiltable gantry, and apparatus and method for tilting a gantry, will become apparent by reference to the following detailed description taken in connection with the accompanying drawings.

DETAILED DESCRIPTION OF DISCLOSURE

Referring to FIGS. 1 through 5, wherein like elements throughout the figures are indicated by like reference numerals, a frame 10 according to the present disclosure for an x-ray tomography system is shown. The frame 10 includes a tiltable gantry 12 and unique means 14 for tilting the gantry 12 such that a relatively small force is required to tilt the gantry 12.

In addition to the annular gantry 12, the frame 10 includes a stand 16 having two arms 18, 20. The annular gantry 12 is positioned between the two arms 18, 20 and has an outer support 22 pivotally mounted to the arms 18, 20 of the stand 16 for tilting of the gantry 12 about a tilt axis "T" extending between the arms 18, 20 and through the center of the gantry. An inner support 24 is rotatable within and with respect to the outer support 22 about a spin axis "S" of the gantry 12, the spin axis "S" being substantially normal to the tilt axis "T". The inner support 24 is adapted to hold x-ray tomography components for rotation therewith.

Figure 1:
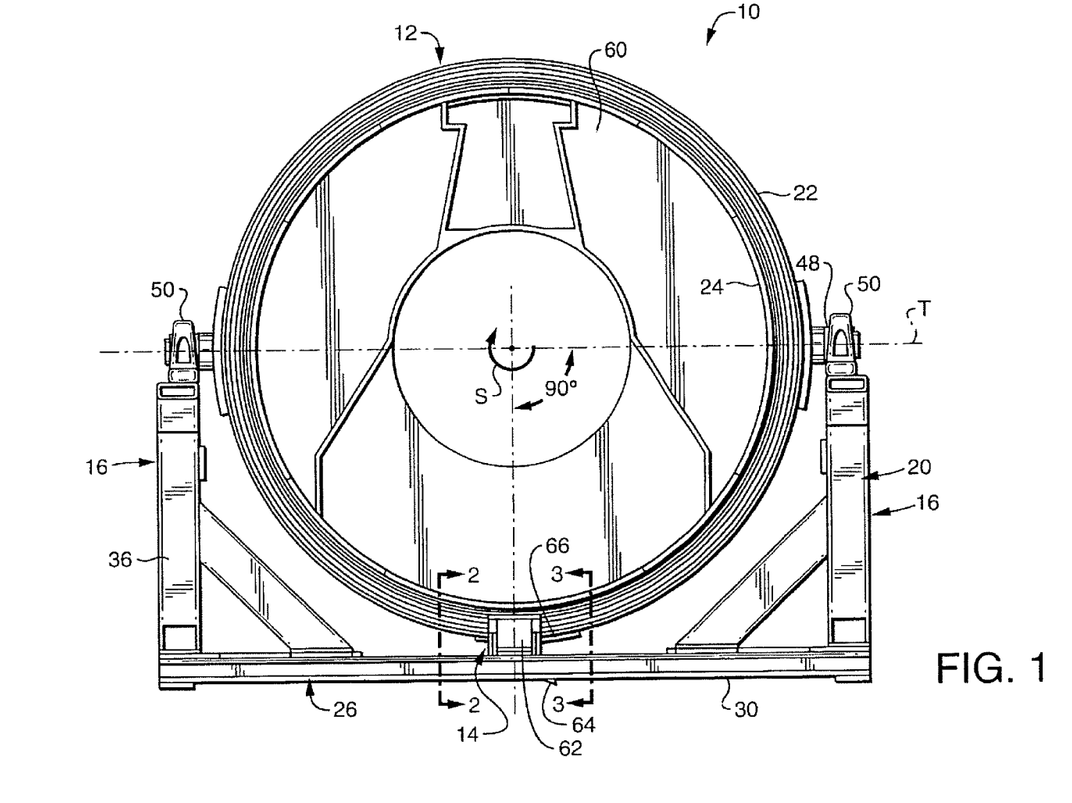
FIG. 1 is a front elevation view of a frame according to the present disclosure for use as part of an x-ray tomography system.
Figure 2:
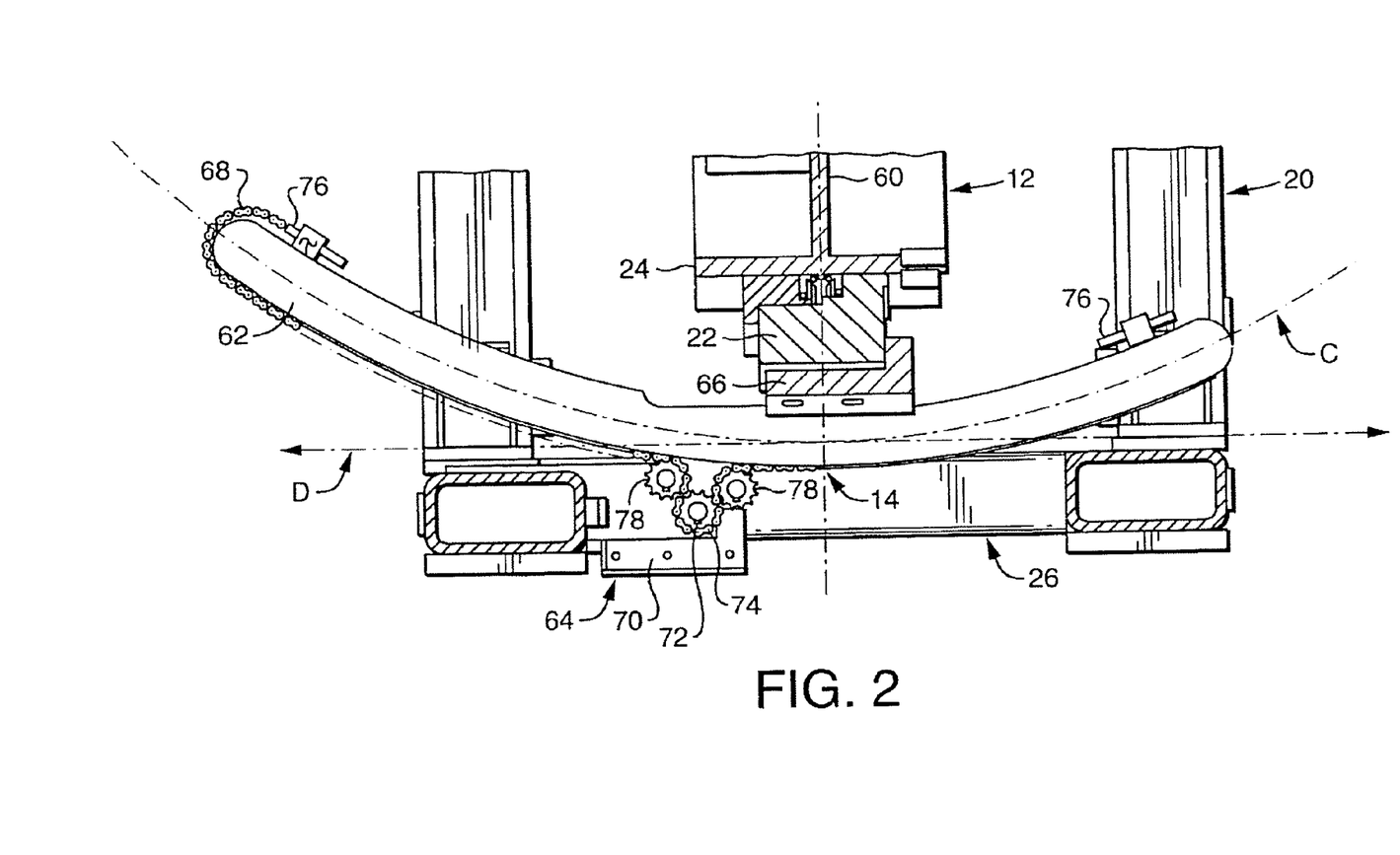
FIG. 2 is a sectional view of a portion of the frame taken along lines 2—2 of FIG. 1.
Figure 3:
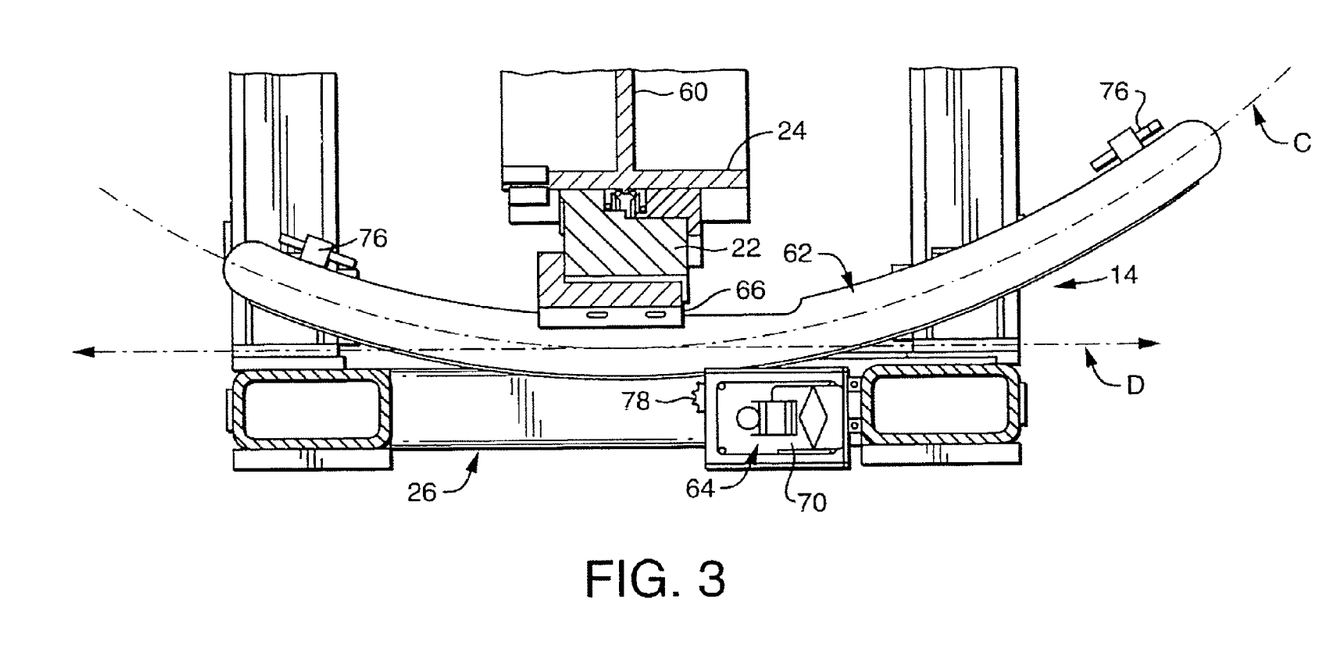
FIG. 3 is a sectional view of a portion of the frame taken along lines 3—3 of FIG. 1.
Figure 4:
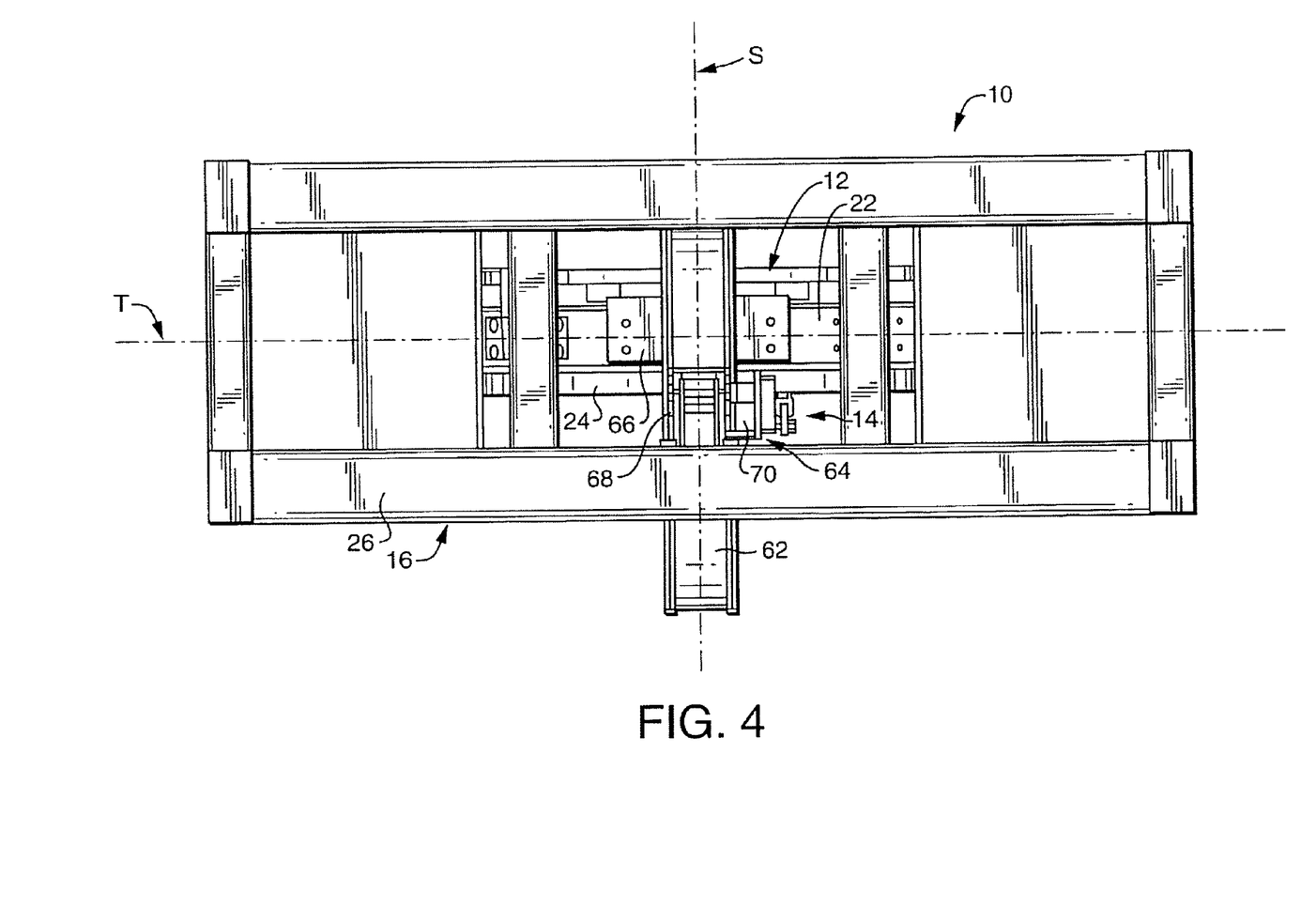
FIG. 4 is a bottom plan view of the frame of FIG. 1.

Still referring to FIGS. 1–5, the means 14 for tilting the gantry 12 applies a force to a substantially outermost circumference of the gantry 12 so as to effect tilting of the gantry 12 about the tilt axis "T" with a minimum amount of force. Preferably, the force is applied to the gantry 12 in a direction "D", as shown in FIGS. 2 and 3, substantially parallel to the spin axis "S" of the gantry 12. In addition, the force is preferably applied to a substantially outermost circumference of the gantry 12 about ninety degrees from the tilt axis "T", as shown in FIG. 1.

Because the means 14 for tilting the gantry 12 applies a force to a substantially outermost circumference of the gantry 12, sufficient torque is created for tilting the gantry 12 with a minimum amount of force (excluding attaching some form of torque arm to the gantry that extends beyond the outermost circumference of the gantry). In addition, since the means 14 for tilting the gantry 12 preferably applies the force in a direction "D" substantially parallel to the spin axis "S" of the gantry 12, and at about ninety degrees from the tilt axis "T", as shown in FIG. 1, the force is applied most efficiently. In fact, it has been found that a motor 70 for tilting the gantry 12, as discussed in greater detail below, need only be capable of producing about 0.1 horsepower.

The means 14 for tilting the gantry 12 preferably comprises a tilt guide 62 secured to one of the gantry 12 and the stand 16 at the outermost circumference of the gantry, and about ninety degrees from the tilt axis "T"; and a drive mechanism 64 secured to the other of the gantry 12 and the stand 16 for driving the tilt guide 62 in the direction "D" substantially parallel to the spin axis "S" of the gantry 12.

In the particular embodiment shown, the tilt guide 62 is secured to the gantry 12 and the drive mechanism 64 is secured to the stand 16. It should be appreciated, however, that the tilt guide 62 could be secured to the stand 16 and the drive mechanism 64 secured to the gantry 12. Preferably, the tilt guide 62 is provided with an arcuate or circular shape "C", as shown in FIGS. 2–3, having a center of curvature on the tilt axis "T" of the gantry 12, such that the tilt guide 62 can follow the arcuate path of the outer circumference of the gantry 12 as the gantry is tilted.

The tilt guide 62 is secured to the outer support 22 of the gantry 12 through a block 66. The drive mechanism 64 comprises a chain 68 secured to the arcuate tilt guide 62, and a motor 70 including a drive shaft 72 and a sprocket 74 fixed to the drive shaft. Preferably, the motor 70 comprises an electric reversible stepping motor. As shown, the drive sprocket 74 meshes with the chain 68 for driving the tilt guide 62 upon rotation of the drive shaft 72 of the motor 70. Preferably, the chain 68 is adjustably secured to the tilt guide 62, using anchored screws 76, for example, and the motor 70 is also provided with idler sprockets 78 on either side of the drive sprocket 74 for maintaining the chain 68 on the drive sprocket. As an alternative to the chain 68, for example, the tilt guide 62 itself could be provided with a gear-like surface having teeth for directly meshing with the drive sprocket 74 of the motor 70.

It should be understood that alternative means 14 for applying a force to a substantially outermost circumference of the gantry 12 may be incorporated into the presently disclosed frame 10 without departing from the spirit and scope of the appended claims. For example, the means 14 could alternatively comprise a ball nut secured to one of the stand 16 and the gantry 12 and an elongated, straight screw element and a reversible motor secured to the other of the stand 16 and the gantry 12. The ball nut would be secured at the substantially outermost circumference of the gantry 12. The straight screw element should be suitably journaled so that the screw element can also pivot in order to accommodate the arcuate path of the outer circumference of the gantry 12 as the gantry tilts.

Although not shown, the frame 10 can also include means for measuring the amount of tilt of the gantry 12 such as, for example, a potentiometer suitably biased with a supply voltage for providing a voltage output as a function of the position of the arcuate tilt guide 62. Such a potentiometer based electro-mechanical measuring apparatus is shown and described in U.S. Pat. No. Re. 36,415 to McKenna, entitled "X-ray Tomography System with Gantry Pivot and Translation Control", the disclosure of which is incorporated herein by reference in its entirety. In that patent, McKenna shows an x-ray tomography system wherein tilting movement of the gantry is monitored using a potentiometer.

A similar potentiometer can be secured between the stand 16 and the arcuate tilt guide 62 to provide an extremely precise voltage signal indicative of any movement of the tilt guide 62 with respect to the stand (and thus tilting movement of the gantry 12). The amount of tilting of the gantry 12 can then be measured and displayed by conventional means for interpreting the voltage across the potentiometer.

The present disclosure also provides a method of conducting x-ray tomography. The method includes positioning a subject (not shown) to be x-rayed coaxially within the annular gantry 12 of an x-ray tomography system incorporating the frame 10, so that the subject substantially intersects the spin axis "S" of the gantry 12. The inner support 24 of the gantry 12 is then rotated about the spin axis "S", x-rays are emitted radially inwardly from the rotating inner support 24 so that the x-rays are focused on the spin axis "S", and the x-rays passing through the subject are detected. The method also includes applying a force to a substantially outermost circumference of the gantry 12 prior to emitting x-rays so as to effect tilting of the gantry about the tilt axis "T" until the spin axis "S" of the gantry is substantially aligned with the subject.

Preferably, in addition to applying the force to a substantially outermost circumference of the gantry 12, the force is applied in the direction "D", shown in FIGS. 2 and 3, substantially parallel to the spin axis "S", and is applied about ninety degrees from the tilt axis "T" of the gantry 12, as shown in FIG. 1.

Figure 5:
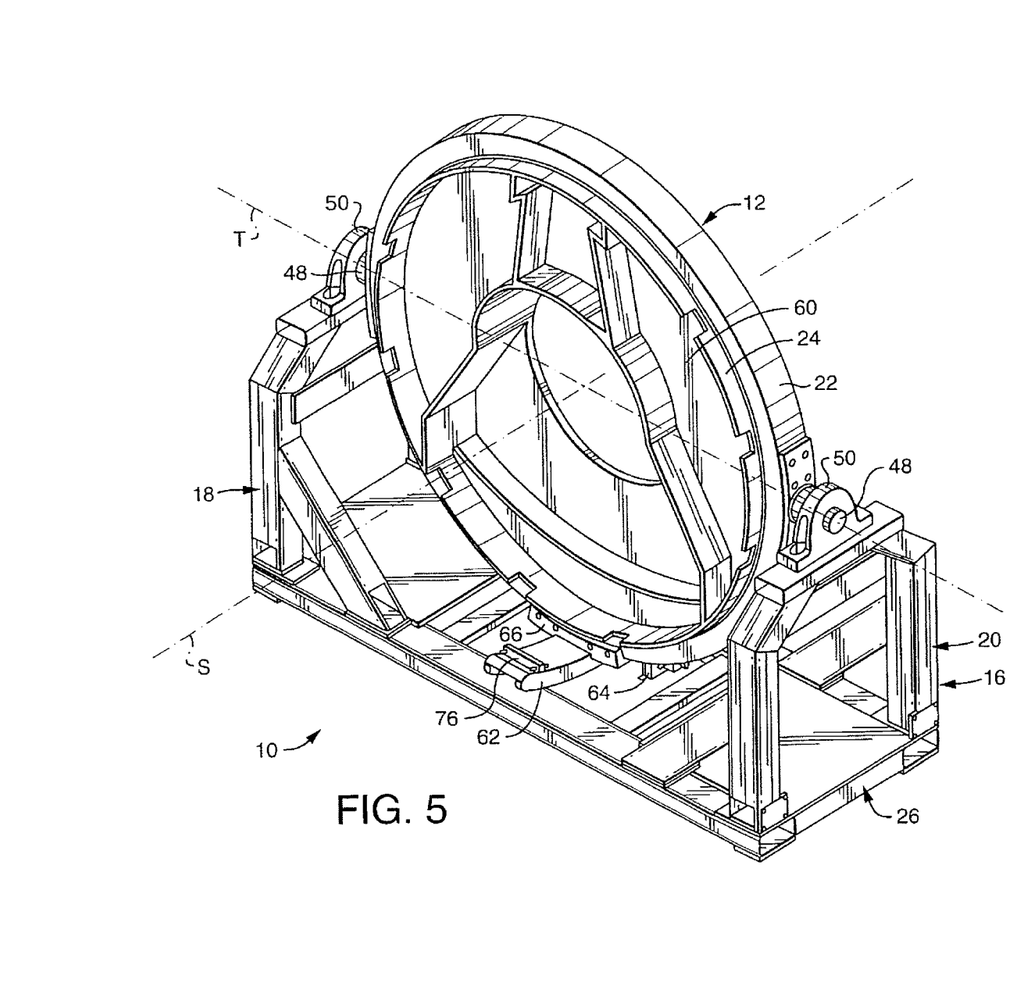
FIG. 5 is an isometric view of the frame of FIG. 1.

It should be understood that the particular configurations of the stand 16 and the gantry 12 are not important to the present disclosure, since the tilting mechanism and method disclosed herein can be applied and used with many different types of tiltable gantries mounted on stands. As best seen in FIGS. 1 and 5, however, the stand 16 is generally of a U-shaped configuration and includes a horizontal base 26 from which the arms 18, 20 extend upwardly from opposite ends of the base. The motor 70 for tilting the gantry 12 is mounted on the base 26.

Referring to FIG. 1, the frame 10 includes means for pivotally mounting the outer support 22 of the gantry 12 to the arms 18, 20 of the stand 16. A preferred means includes beams 48 secured to one of the outer support 22 and the arms 18, 20, and bearings 50 secured to the other of the gantry and the arms, and receiving and supporting the beams 48 such that the beams 48 can be rotated. In the particular embodiment of the frame 10, as shown in FIG. 1, the bearings 50 are secured on the arms 18, 20, and the beams 48 are secured to an outer circumference of the outer support 22 of the gantry 12 such that the beams 48 extend radially outwardly from opposite sides of the gantry 12. The tilt axis "T" of the gantry 12 passes through the axes of both beams 48.

Both the outer and the inner supports 22, 24 of the annular gantry 12 can be formed as continuous rings, as shown in FIGS. 1 and 5. The inner support or ring 24 is able to rotate with respect to the outer support or ring 22 about the spin axis "S" of the gantry 12. Other than rotating about the spin axis "S", the inner support 24 is not able to move relative to the outer support 22. In general, the inner support 24 includes a radially inwardly extending annular mounting plate 60 configured for receiving and supporting conventional x-ray tomography components, such as an x-ray tube assembly, a plurality or array of x-ray detectors positioned diametrically opposite the x-ray tube assembly, and a power source. The components secured to the annular mounting plate 60 will of course rotate with the inner support 24 about the spin axis "S". Although not shown, a skin or cover of x-ray transparent material, such as a polycarbonate plastic or the like, may be provided and secured in place over the gantry 12 to protect and conceal the components contained therein. A cover or rigid shell may also be provided for the stand 16.

Figure 6:
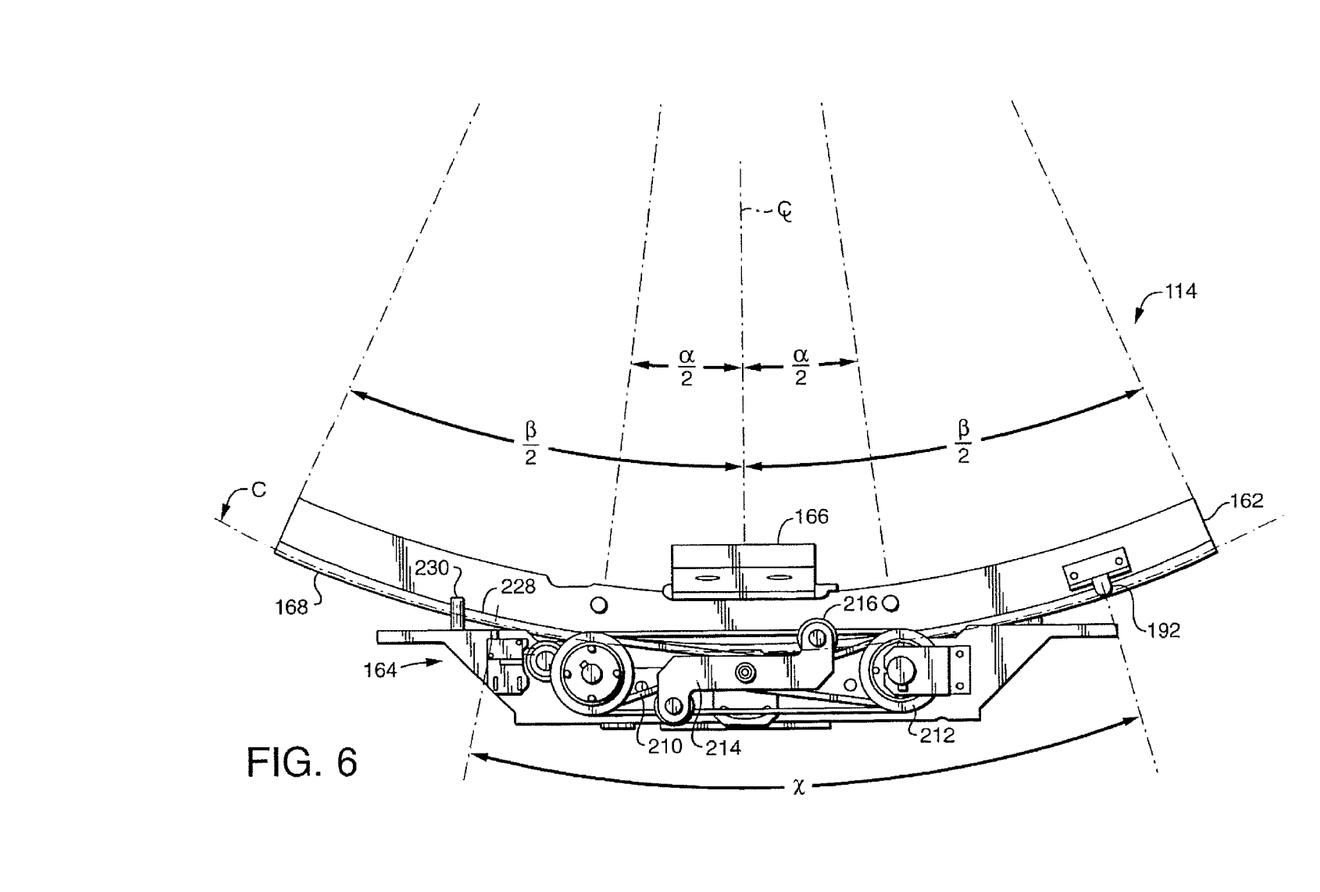
FIG. 6 is a side elevation view of an apparatus according to the present disclosure for tilting a gantry of an x-ray tomography system, wherein the apparatus includes a rocker for attachment to a gantry and a drive mechanism for attachment to a base of an x-ray tomography system and for driving the rocker to tilt the gantry.
Figure 7:
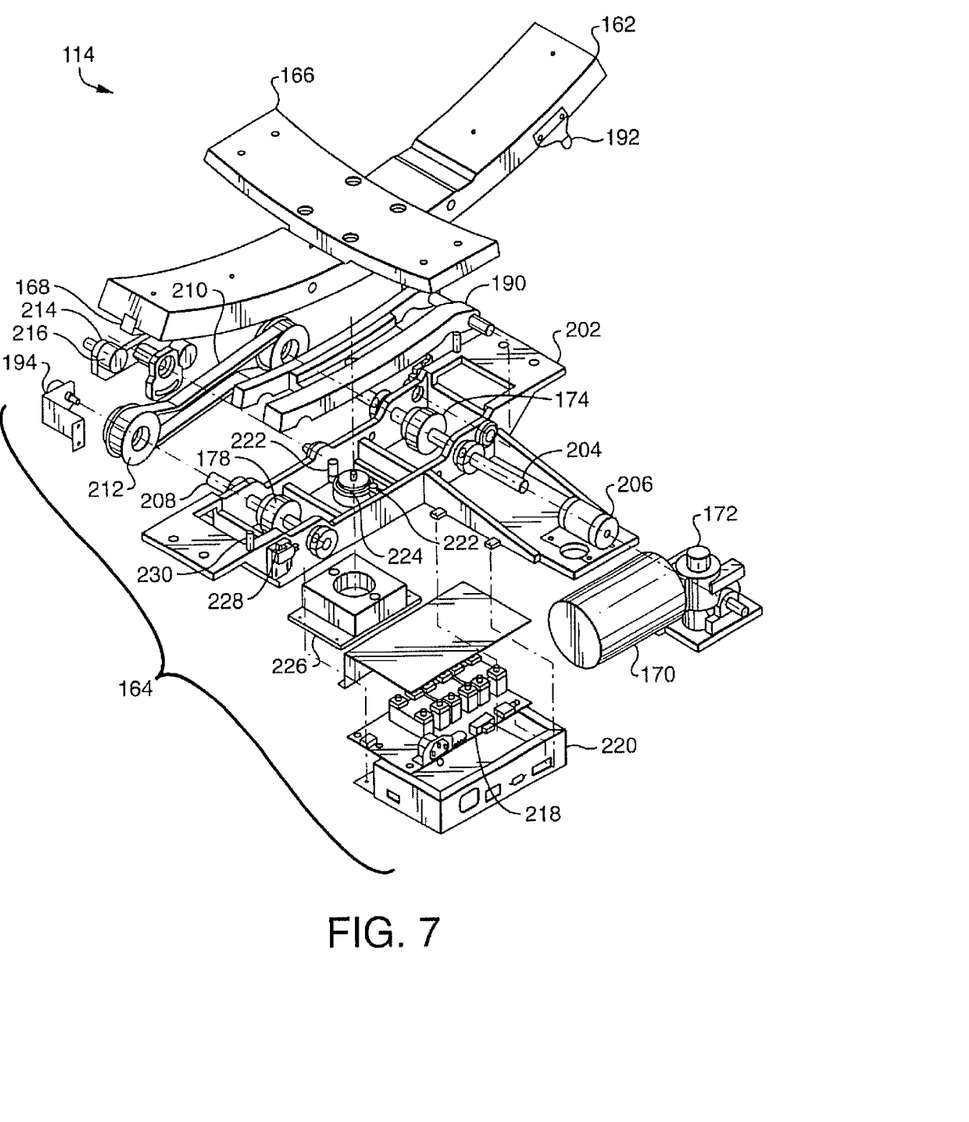
FIG. 7 is a side and top isometric, exploded view of the apparatus of FIG. 6.
Figure 8:
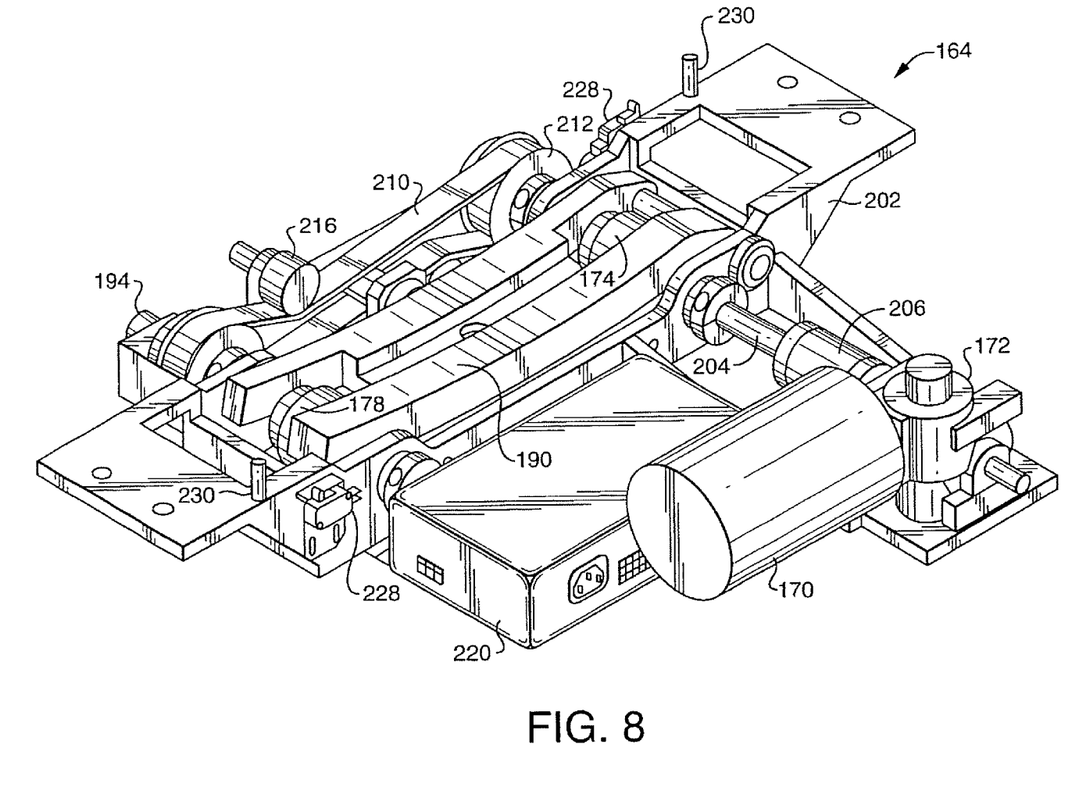
FIG. 8 is a side and top isometric view of the drive mechanism of the apparatus of FIG. 6.
Figure 9:
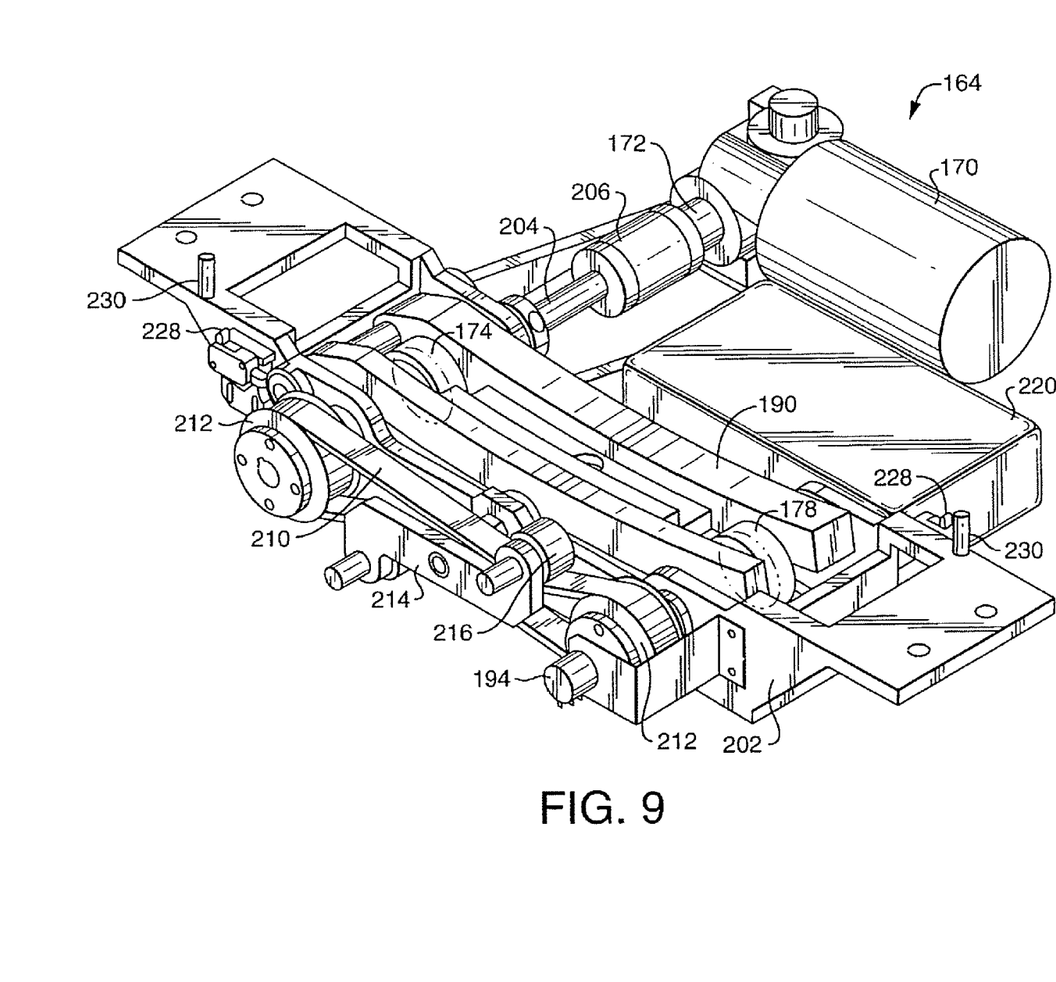
FIG. 9 is an opposite side and top isometric view of the drive mechanism of the apparatus of FIG. 6.
Figure 10:
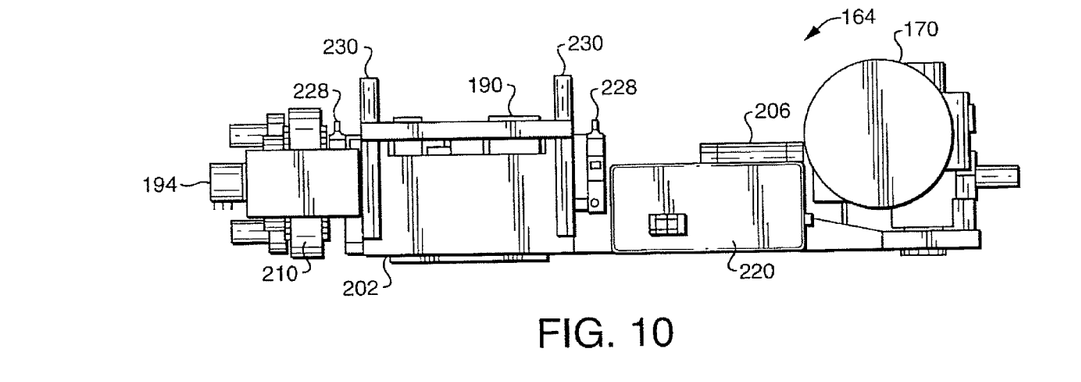
FIG. 10 is an end elevation view of the drive mechanism of the apparatus of FIG. 6.
Figure 11:
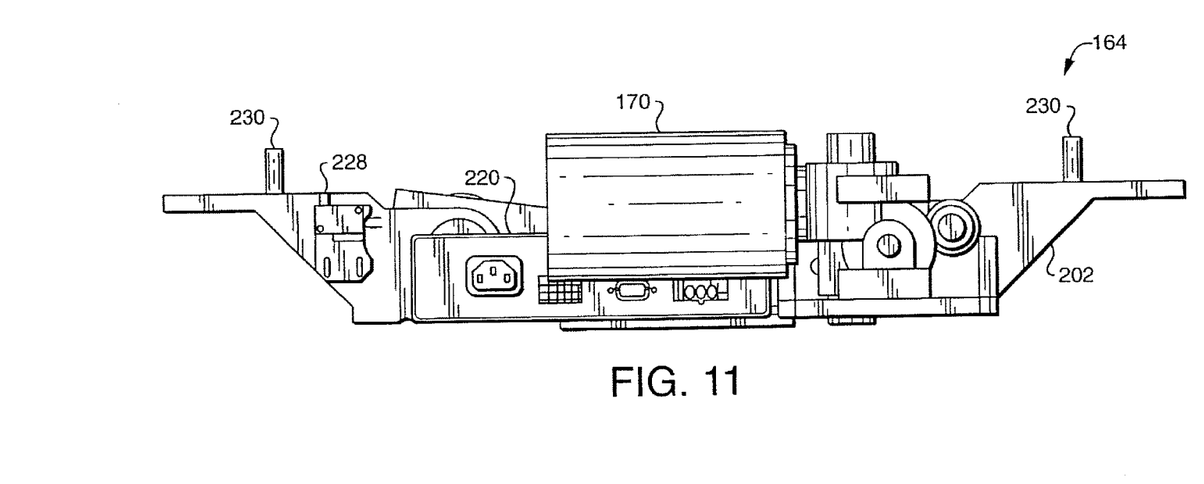
FIG. 11 is a side elevation view of the drive mechanism of the apparatus of FIG. 6.
Figure 12:
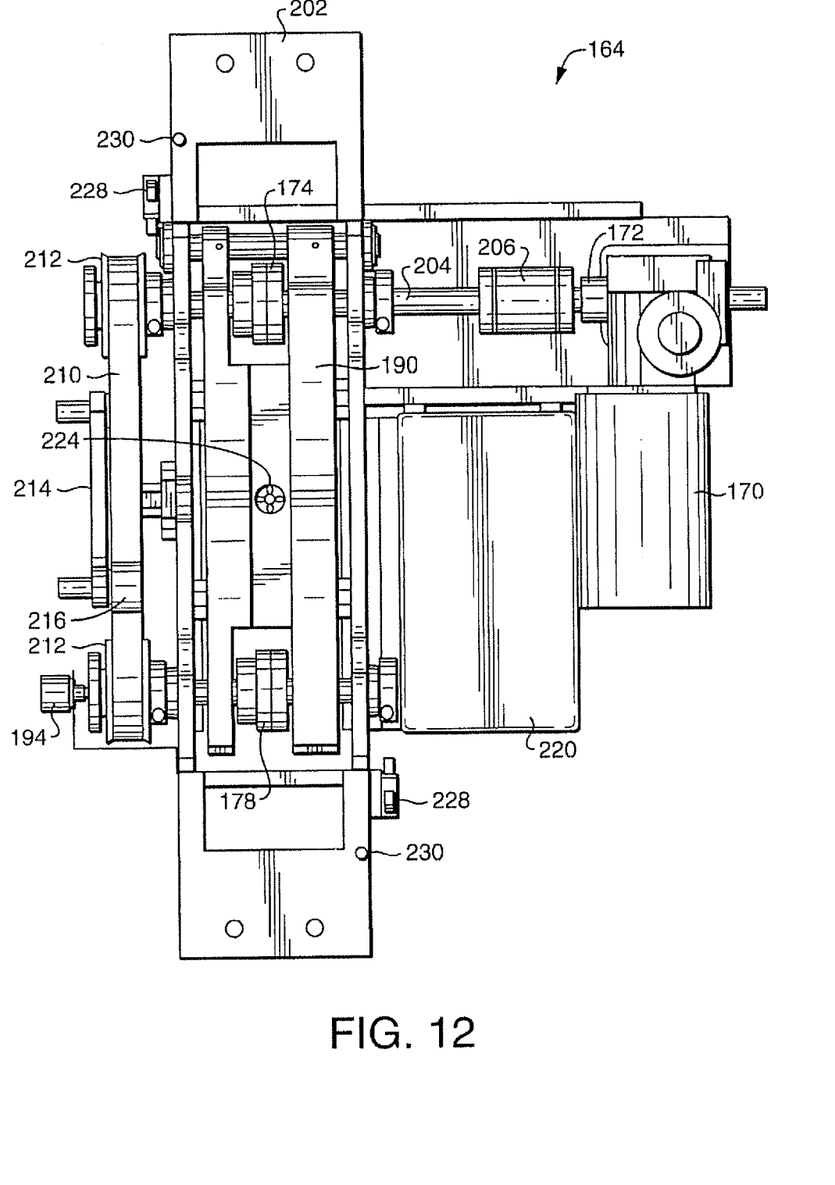
FIG. 12 is a top plan view of the drive mechanism of the apparatus of FIG. 6.

Referring now to FIGS. 6 and 7, the present disclosure provides an additional apparatus 114 for tilting a gantry of an x-ray tomography system. The apparatus 114 is similar to the apparatus 14 of FIGS. 1–5 such that similar elements have the same reference numerals preceded by a "1". The apparatus 114 of FIGS. 6 and 7, however, additionally includes a tilt lock 190, a tilt limiter 192, and a tilt monitor 194. In addition, the apparatus 114 of FIGS. 6 and 7 allows the use of a tilt guide 162 having a relatively short length, thereby ensuring that the apparatus 114 fits within a typical frame and housing of a CT scanner.

The following discussion of the apparatus 114 of FIGS. 6 through 12 includes references to the x-ray tomography frame 10 of FIG. 5. The apparatus 114 includes the tilt guide 162 and a drive mechanism 164. The tilt guide 162 is securable to one of the gantry 12 and the stand 16 of the x-ray tomography frame 10, while the drive mechanism 164 is securable to the other of the gantry 12 and the stand 16. In the particular embodiment shown, the tilt guide 162 is adapted for being secured to the gantry 12, and the drive mechanism 164 is adapted for being secured to the stand 16. It should be appreciated, however, that the tilt guide 162 could be secured to the stand 16 and the drive mechanism 164 secured to the gantry 12.

Preferably, the tilt guide 162 is provided with an arcuate or circular shape "C", as shown in FIG. 6, having a center of curvature corresponding to the tilt axis "T" of the gantry 12, such that the tilt guide 162 follows the arcuate path of the outer circumference of the gantry 12 as the gantry is tilted. The tilt guide 162 is secured to the outer support 22 of the gantry 12 through a block 166.

In particular, the tilt guide 162 is secured at the outermost circumference of the gantry, and about ninety degrees from the tilt axis "T". The drive mechanism 164 applies force to the tilt guide 162 in a direction tangential to the arcuate path "C", such that a minimum amount of force is required for tilting.

The drive mechanism 164 includes two spaced apart drive wheels 174, 178. In the particular embodiment shown, the drive wheels comprise sprockets 174, 178 having teeth. The teeth of each sprocket 174, 178 operatively engage the tilt guide 162 such that turning the sprockets applies the substantially tangential force to the tilt guide 162 to tilt the gantry 12 about the tilt axis "T". Because the sprockets 174, 178 are spaced-apart and at least one of the sprockets engages the tilt guide 162 at all times, a shorter tilt guide 162 can be used. The two sprockets 174, 178 are preferably spaced by an angle α equal to about 15° with respect to the center of curvature of the tilt guide 162, while the tilt guide has an arcuate length β along the curvature "C" equal to about 48° with respect to the center of curvature, as shown in FIG. 6. Thus, after more than ±16.5° of tilting, only one of the sprockets 174, 178 continues to engage the tilt guide 162. While only two sprockets 174, 178 are used with the particular apparatus 114 of FIGS. 6–12, the apparatus can be provided with more than two sprockets.

The tilt guide 162 includes, in a groove of a bottom surface of the guide, a gear-like insert 168 having teeth for directly meshing with teeth of the sprockets 174, 178. Alternatively, the tilt guide 162 could be provided with a chain for meshing with the sprockets, similar to the tilt guide 62 of FIG. 2. The gear-like insert 168 extends between opposing ends of the guide 162.

A housing 202 is provided for securing the drive mechanism 164 to the frame 10 of the x-ray tomography system. The drive mechanism 164 also includes a motor 170 mounted to the housing 202 for turning the sprockets 174, 178, which are rotatably mounted within the housing 202. A drive shaft 172 of the motor 170 is directly connected to a shaft 204 of a first of the sprockets 174 through a coupling 206, and indirectly connected to a shaft 208 of a second of the sprockets 178 through a drive belt 210. The continuous drive belt 210 extends around pulleys 212 attached to the shafts 204, 208 of the sprockets 174, 178. The drive mechanism 164 also includes a tensioning assembly 214 secured to the housing 202 and including two rollers 216 for maintaining the belt 210 in tension around the pulleys 212.

The apparatus 114 is provided with a computer control unit 218 contained in a case 220, which is secured to the housing 202. The control unit 218 supplies power to the motor 170 and is programmed to control operation of the motor 170 through the supply of power. The control unit 218 is also programmed to receive and follow instructions provided by a main controller (not shown) of an x-ray tomography system employing the tilt apparatus 114.

The tilt lock 190 is movable against the tilt guide 162 to hold the tilt guide in a fixed vertical or tilted position. In the particular embodiment shown, the lock 190 is pivotally mounted to the housing 202, and biased against the tilt guide 162 with compression springs 222. The lock 190 also has a release device 224 for moving the lock away from the tilt guide. The release device preferably comprises an actuator connected to the tilt lock 190, and in particular an electrical solenoid 224 that pulls the tilt lock away from the tilt guide 162 when actuated. The solenoid 224 is secured to the housing 202 with a mounting block 226 that also acts as a heat sink for the solenoid. The control unit 218 is programmed to supply power to the solenoid 224, and release the tilt guide 162, upon providing power to the tilt motor 170, and is programmed to stop supplying power to the solenoid 224 and lock the tilt guide 162 in position upon stopping the tilt motor 170.

The tilt limiter 192 is attached to one of the tilt guide 162 and the drive mechanism 164 and, as its name implies, prevents further tilting of the gantry 12 upon the gantry reaching a predetermined maximum extent of tilt $\chi$, as shown in FIG. 6. A tilt limit switch 228 is mounted on the other of the tilt guide 162 and the drive mechanism 164 and is positioned such that the tilt limiter 192 activates the tilt switch 228 upon the gantry 12 reaching the predetermined maximum extent of tilt $\chi$. The tilt limit 228 switch is connected to the control unit 218, which is programmed to stop the tilt motor 170 upon the tilt limit switch 228 being activated.

In the particular apparatus 114 shown, two sets of tilt limiters 192 and tilt limit switches 228 are employed. The limit switches 228 are secured on opposite sides of the housing 202 of the drive mechanism 164, while the tilt limiters 192 are secured on opposite sides of the tilt guide 162 adjacent opposite ends of the tilt guide for actuating their respective switch. The tilt limiters 192 and the switches 228 are preferably arranged such that the tilt limiters activate the switches upon the gantry 12 reaching a predetermined maximum extent of tilt $\chi$ equal to about ± 30.5°, as shown in FIG. 6.

The apparatus 114 preferably also includes tilt limit stops 230 attached to opposite sides of the housing 202 of the drive mechanism 164, just outside of the limit switches 228, for physically preventing further movement of the tilt limiters 192, and thus the tilt guide 162, once the limiters 192 have passed the limit switches 228 during tilting of the gantry 12. As shown, the tilt limiters 192 are provided in the form of brackets which extend outwardly and downwardly from the tilt guide 162.

As its name implies, the tilt monitor 194 provides an indication of the amount of tilting of the gantry 12. In particular, the tilt monitor 194 provides the number of revolutions made by at least one of the sprockets 174, 178, such that the amount of tilting produced by the apparatus 114 can be determined. In the particular apparatus 114 shown, the tilt monitor comprises a potentiometer 194 connected for rotation with the shaft 208 of the second sprocket 178. The potentiometer 194 provides a signal to the control unit 218 of the apparatus 114, which is programmed to calculate the amount of tilt of the gantry 12 based on the number of revolutions of the sprocket 178, and provide an output signal indicative of the amount of tilt.

Figure 13:
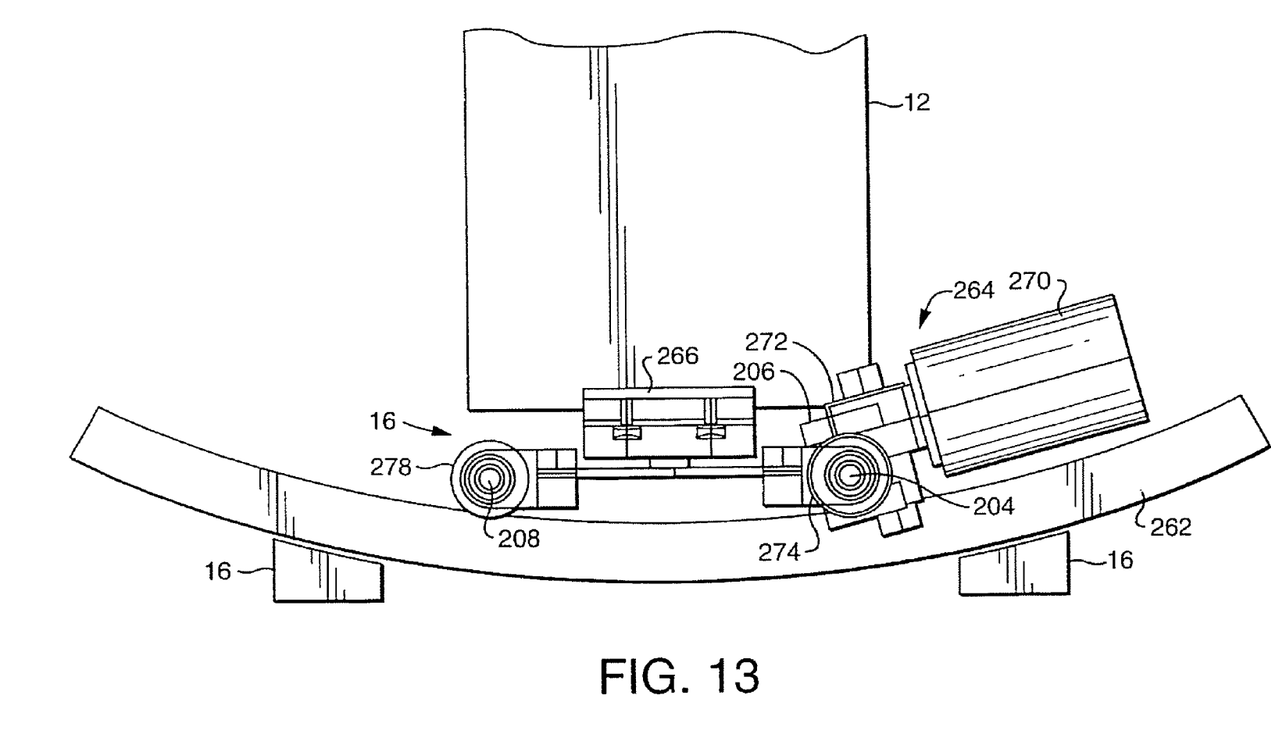
FIG. 13 is a schematic side elevation view of another apparatus according to the present disclosure for tilting a gantry of an x-ray tomography system, wherein the apparatus includes a rocker for attachment to a base of an x-ray tomography system and a drive mechanism for attachment to a gantry for driving along the rocker to tilt the gantry.

Referring to FIG. 13, the present disclosure provides a further apparatus 214 for tilting a gantry 12 of an x-ray tomography system. The apparatus 214 is similar to the apparatus 114 of FIGS. 6 through 12 such that similar elements have the same reference numerals preceded by a "2". The apparatus 214 of FIG. 13, however, includes a tilt guide 262 that is secured to the stand 16 of the x-ray tomography frame 10, while the drive mechanism 264 is secured to the gantry 12. The drive mechanism 264 is secured to the outer support 22 of the gantry 12 through a block 266.

The drive mechanism 264 includes two spaced apart drive wheels 274, 278. Each drive wheel 274, 278 comprises a rubber tire that frictionally contacts the tilt guide 262 such that turning the wheels applies the substantially tangential force to the tilt guide 262 to tilt the gantry 12 about the tilt axis "T". Because the drive wheels 274, 278 are spaced-apart and at least one of the drive wheels 274, 278 engages the tilt guide 262 at all times, a shorter tilt guide 262 can be used. While only two drive wheels 274, 278 are used with the particular apparatus 214 of FIG. 13, the apparatus can be provided with more than two drive wheels.

The drive mechanism 264 also includes a motor 270 mounted to the block 266 for turning the drive wheels 274, 278. A drive shaft 272 of the motor 270 is directly connected to a shaft 204 of a first of the wheels 274 through a coupling 206, and indirectly connected to a shaft 208 of a second of the wheels 278, through a drive belt (not shown) for example.

Because certain changes may be made to the above-described x-ray tomography frame without departing from the spirit and scope of the present disclosure, all matter contained in the above description or shown in the accompanying drawings shall be interpreted in an illustrative and not a limiting sense. The spirit and scope of a frame, a tilting gantry, apparatus for tilting a gantry, an x-ray tomography system, and a method of conducting x-ray tomography, all according to the present disclosure, are defined in the appended claims.

What is claimed is:

1. A frame comprising:
   a) a stand including two substantially upright arms;
   b) a gantry positioned between and pivotally mounted to the arms of the stand for tilting about a tilt axis extending between the arms;
   c) a tilt guide secured to one of the gantry and the stand; and
   d) at least two spaced-apart wheels, each wheel operatively engaging the tilt guide such that turning the wheels applies a force to the tilt guide so that the gantry tilts about the tilt axis.

2. A frame according to claim 1, wherein the tilt guide is secured to one of the gantry and the stand at a substantially outermost portion of the gantry and at about ninety degrees from the tilt axis.

3. A frame according to claim 1, wherein the tilt guide is arcuate and has a center of curvature corresponding to the tilt axis of the gantry.

4. A frame according to claim 1, wherein the tilt guide is arcuate and has a center of curvature corresponding to the tilt axis of the gantry, and the force applied to the tilt guide by each wheel is substantially tangential to the curvature of the tilt guide.

5. A frame according to claim 1, further comprising a motor for turning the wheels.

6. A frame according to claim 5, wherein the motor is directly connected to at least one of the wheels and indirectly connected to the other of the wheels.

7. A frame according to claim 6, wherein the motor is indirectly connected to the other of the wheels through a belt.

8. A frame according to claim 1, further comprising a tilt monitor providing a signal indicative of the number of revolutions made by at least one of the wheels.

9. A frame according to claim 8, wherein the tilt monitor comprises a potentiometer.

10. A frame according to claim 9, further comprising a computer programmed to calculate the extent of tilt of the gantry about the tilt axis based upon the signal provided by the tilt monitor.

11. A frame according to claim 1, further comprising a tilt lock movable against the tilt guide to hold the tilt guide and the gantry stationary about the tilt axis.

12. A frame according to claim 11, further comprising a spring biasing the tilt lock against the tilt guide and an actuator connected to the tilt lock for moving the tilt lock away from the tilt guide.

13. A frame according to claim 1, further comprising:
a tilt limit switch attached to one of the stand and the gantry; and
a tilt limiter attached to the other of the stand and the gantry and positioned to switch the tilt limit switch upon the gantry reaching a predetermined maximum extent of tilt.

14. A frame according to claim 1, further comprising:
a tilt limit stop attached to one of the stand and the gantry; and
a tilt limiter attached to the other of the stand and the gantry and positioned so that the tilt limit stop prevents further movement of the tilt limiter upon the gantry reaching a predetermined maximum extent of tilt about the tilt axis.

15. A frame according to claim 1, wherein the tilt guide is arcuate and has a center of curvature corresponding to the tilt axis of the gantry, and the tilt guide has an arcuate length equal to about 48° with respect to the center of curvature.

16. A frame according to claim 1, wherein the tilt guide is arcuate and has a center of curvature corresponding to the tilt axis of the gantry, and the at least two wheels are spaced about 15° apart with respect to the center of curvature.

17. A frame according to claim 1, wherein the tilt guide is secured to the gantry.

18. A frame according to claim 1, wherein the tilt guide is secured to the stand.

19. A frame according to claim 1, wherein the wheels of the drive mechanism comprise sprockets having teeth and the tilt guide includes teeth directly meshing with the teeth of the sprockets.

20. A frame according to claim 1, wherein the wheels of the drive mechanism comprise tires frictionally engaging a surface of the tilt guide.

21. A frame comprising:
a) a stand including two substantially upright arms;
b) a gantry positioned between and pivotally mounted to the arms of the stand for tilting about a tilt axis extending between the arms;
c) a tilt guide secured to one of the gantry and the stand at a substantially outermost portion of the gantry and at about ninety degrees from the tilt axis for tilting the gantry about the tilt axis upon a force applied to the tilt guide; and
d) a tilt lock movable against the tilt guide to hold the tilt guide in a fixed position.

22. A frame according to claim 21, further comprising a spring biasing the tilt lock against the tilt guide and an actuator for moving the tilt lock away from the tilt guide.

23. A frame according to claim 21, further comprising:
a tilt limit switch attached to one of the stand and the gantry; and
a tilt limiter attached to the other of the stand and the gantry and positioned to switch the tilt limit switch upon the gantry reaching a predetermined maximum extent of tilt.

24. A frame according to claim 21, further comprising:
a tilt limit stop attached to one of the stand and the gantry; and
a tilt limiter attached to the other of the stand and the gantry and positioned so that the tilt limit stop prevents further movement of the tilt limiter upon the gantry reaching a predetermined maximum extent of tilt about the tilt axis.

25. A frame according to claim 21, wherein the tilt guide is secured to the gantry.

26. A frame according to claim 21, wherein the tilt guide is secured to one of the gantry and the stand at a substantially outermost portion of the gantry and at about ninety degrees from the tilt axis.

27. A frame according to claim 21, wherein the tilt guide is arcuate and has a center of curvature corresponding to the tilt axis of the gantry.

28. A frame according to claim 21, wherein the tilt guide is secured to the gantry.

29. A frame according to claim 21, wherein the tilt guide is secured to the stand.

30. A frame according to claim 21, wherein the wheels of the drive mechanism comprise sprockets having teeth and the tilt guide includes teeth directly meshing with the teeth of the sprockets.

31. A frame according to claim 21, wherein the wheels of the drive mechanism comprise tires frictionally engaging a surface of the tilt guide.

32. An apparatus for tilting a gantry about a tilt axis extending between arms of a stand, comprising;
A.) a tilt guide securable to one of the gantry and the stand, and wherein the tilt guide is arcuate and has a center of curvature corresponding to the tilt axis of the gantry; and
B.) a drive mechanism securable to the other of the gantry and the stand, the drive mechanism including at least two wheels spaced less than a length of the tilt guide, each of the wheels for operatively engaging the tilt guide such that turning the wheels applies a substantially tangential force to the tilt guide for tilting the gantry about the tilt axis.

33. An apparatus according to claim 32, wherein the at least two wheels are spaced about 15° apart with respect to the center of curvature of the tilt guide.

34. An apparatus according to claim 33, wherein the tilt guide has an arcuate length equal to about 48°.

35. An apparatus according to claim 32, further comprising a motor for turning the wheels.

36. An apparatus according to claim 35, wherein the motor is directly connected to at least one of the wheels and indirectly connected to the other of the wheels.

37. An apparatus according to claim 32, further comprising a tilt lock movable against the tilt guide to hold the tilt guide in a fixed position.

38. An apparatus according to claim 37, further comprising a spring biasing the tilt lock against the tilt guide and an actuator for moving the tilt lock away from the tilt guide.

39. An apparatus according to claim 32, further comprising:
   a tilt limit switch attached to one of the tilt guide and the drive mechanism; and
   a tilt limiter attached to the other of the tilt guide and the drive mechanism and positioned to switch the tilt limit switch upon the gantry reaching a predetermined maximum extent of tilt.

40. An apparatus according to claim 32, further comprising:
   a tilt limit stop attached to one of the tilt guide and the drive mechanism; and
   a tilt limiter attached to the other of the tilt guide and the drive mechanism and positioned so that the tilt limit stop will prevent further movement of the tilt limiter upon the gantry reaching a predetermined maximum extent of tilt about the tilt axis.

41. An apparatus according to claim 32, wherein the tilt guide is secured to the gantry.

42. An apparatus according to claim 32, wherein the tilt guide is secured to the stand.

43. An apparatus according to claim 32, wherein the wheels of the drive mechanism comprise sprockets having teeth and the tilt guide includes teeth directly meshing with the teeth of the sprockets.

44. An apparatus according to claim 32, wherein the wheels of the drive mechanism comprise tires frictionally engaging a surface of the tilt guide.

* * * * *